United States Patent
Myers

(10) Patent No.: US 9,216,277 B2
(45) Date of Patent: Dec. 22, 2015

(54) HEMOSTASIS MECHANISM AND METHOD

(71) Applicant: Randy Joe Myers, Bloomington, IN (US)

(72) Inventor: Randy Joe Myers, Bloomington, IN (US)

(73) Assignee: Cook Medical Technologies, LLC, Bloomington, IN (US)

( * ) Notice: Subject to any disclaimer, the term of this patent is extended or adjusted under 35 U.S.C. 154(b) by 215 days.

(21) Appl. No.: 13/769,510

(22) Filed: Feb. 18, 2013

(65) Prior Publication Data

US 2013/0253565 A1 Sep. 26, 2013

Related U.S. Application Data

(60) Provisional application No. 61/613,120, filed on Mar. 20, 2012.

(51) Int. Cl.
*A61M 5/178* (2006.01)
*A61M 39/06* (2006.01)
*A61M 25/10* (2013.01)
*A61M 29/02* (2006.01)

(52) U.S. Cl.
CPC ..... *A61M 39/0613* (2013.01); *A61M 25/10182* (2013.11); *A61M 29/02* (2013.01); *A61M 2039/062* (2013.01); *A61M 2039/0626* (2013.01); *A61M 2039/0673* (2013.01)

(58) Field of Classification Search
CPC ............ A61M 1/0068; A61M 25/10182; A61M 5/178; A61M 5/315; A61M 5/48; A61M 5/484; A61M 5/488; A61M 5/50; A61M 5/5013; A61M 5/502; A61M 2005/5033; A61M 25/1018; A61M 25/10181; A61M 39/06; A61M 39/0606; A61M 39/0613; A61M 2039/062; A61M 2039/0626; A61M 2039/0673

See application file for complete search history.

(56) References Cited

U.S. PATENT DOCUMENTS

| | | | |
|---|---|---|---|
| 4,960,259 A | 10/1990 | Sunnanväder et al. | |
| 5,127,906 A * | 7/1992 | Landry et al. | 604/110 |
| 5,514,109 A | 5/1996 | Mollenauer et al. | |
| 5,871,474 A | 2/1999 | Hermann et al. | |
| 5,895,376 A | 4/1999 | Schwartz et al. | |
| 6,221,057 B1 | 4/2001 | Schwartz et al. | |
| 6,276,661 B1 | 8/2001 | Laird | |
| 7,597,688 B1 | 10/2009 | Masson | |
| 2001/0021828 A1* | 9/2001 | Fischer et al. | 604/218 |
| 2004/0172008 A1 | 9/2004 | Layer | |
| 2011/0282301 A1 | 11/2011 | Nielson | |

FOREIGN PATENT DOCUMENTS

| | | |
|---|---|---|
| EP | 0307743 | 9/1988 |
| EP | 1046843 A2 | 4/2000 |
| EP | 1046843 A3 | 6/2002 |
| WO | 9911308 | 3/1999 |

* cited by examiner

*Primary Examiner* — Jonathan W Miles
(74) *Attorney, Agent, or Firm* — Liell & McNeil

(57) ABSTRACT

A hemostasis mechanism includes a housing, and a pressure responsive seal positioned within the housing and having an outer seal surface exposed to a fluid pressure of a port formed in the housing. A pressurization device is in fluid communication with the port, and includes a detent having a release state, and an engaged state holding a plunger of the pressurization device at an advanced position to maintain an increased fluid pressure supplied to the pressure responsive seal to maintain sealing engagement about a transluminal device. Related methodology is also disclosed.

17 Claims, 3 Drawing Sheets

HEMOSTASIS MECHANISM AND METHOD

RELATION TO OTHER PATENT APPLICATION

This application claims priority to provisional patent application 61/613,120, filed Mar. 20, 2012 with the same title.

TECHNICAL FIELD

The present disclosure relates generally to fluidly sealing about a transluminal device with a pressure responsive seal in a hemostasis mechanism, and relates more particularly to controlling the fluid sealing via engaging and releasing a detent in a pressurization device.

BACKGROUND

A variety of different sealing mechanisms are used to prevent the backflow of blood or other fluids from a patient during certain types of treatment or diagnostic procedures. In a typical transluminal treatment or diagnostic scenario, a clinician controls such a mechanism to alternately block or open a fluid conduit extending from outside the patient into an intraluminal space such as a vein or artery. Transluminal devices such as wire guides and catheters may be passed through the conduit when open, and backflow of blood or another fluid can be prevented when the conduit is closed. Since it is often necessary for transluminal devices to reside within the fluid conduit when a seal is established, many sealing mechanisms are engineered to fluidly seal around a wire guide, catheter or the like.

One particular strategy employs a push/pull sleeve or tube, coupled with a housing, which can be advanced through the center of a resilient gasket or the like positioned in the housing to open the gasket and provide a passage for introducing a transluminal device into the patient. When the push/pull sleeve is retracted, a fluid seal is formed about the device by way of a tendency for the gasket to return to a closed state. Other techniques employ a rotating mechanism which adjusts a different type of gasket from an open configuration to a closed configuration, sealing about a transluminal device. Each of these strategies has various drawbacks. In the case of rotating mechanism devices, their use can be unwieldy and slow. In certain instances, a clinician may need to seal and unseal about a device multiple times during a procedure, and the need to rotate a sealing mechanism to seal, unseal, seal again, etc. can be tiresome. In the case of push/pull devices, some of these shortcomings do not exist, as forming or unforming a seal is fairly quick and easy. A tradeoff may exist, however, in the robustness of the seal, for at least certain of such designs. In other words, while push/pull designs may be efficient to use, the seal may not be as effective against preventing backflow of fluid from a patient.

Another known strategy is set forth in United States Patent Application Publication Number 2004/0172008 to Layer. Layer proposes a hemostasis valve having a collapsible member positionable within a valve body, and a pressure application system configured to increase a pressure within an elongate chamber in the valve body to seal the collapsible member about a medical instrument. While Layer may be suitable for its intended purposes, the strategy has various shortcomings.

SUMMARY

In one aspect, a hemostasis mechanism for use in treating a patient includes a housing defining a through-bore having a longitudinal axis, and a port in fluid communication with the through-bore. The mechanism further includes a pressure responsive seal extending circumferentially about the longitudinal axis within the through-bore, and having an outer seal surface exposed to a fluid pressure of the port, and an inner seal surface. A pressurization device is in fluid communication with the port, and includes a plunger movable from a first position toward an advanced position, to increase the fluid pressure such that the pressure responsive seal deforms into sealing engagement with a transluminal device positioned within the through-bore. The pressurization device further includes a detent operably coupled with the plunger and having a release state, and an engaged state holding the plunger in the advanced position to maintain the increased fluid pressure.

In another aspect, a method of percutaneously treating a patient includes pushing a plunger toward an advanced position in a pressurization device in fluid communication with a pressure responsive seal of a hemostasis mechanism in sealing engagement with a transluminal device, and adjusting a detent in the pressurization device from an engaged state inhibiting retracting of the plunger, to a release state, in response to the pushing of the plunger. The method further includes retracting the plunger subsequent to adjusting the detent such that a fluid pressure supplied by the pressurization device to the pressure responsive seal is reduced, and sliding the transluminal device through the hemostasis mechanism to change its position within a body lumen of the patient while the fluid pressure is at the reduced pressure.

DETAILED DESCRIPTION

Figure 1:
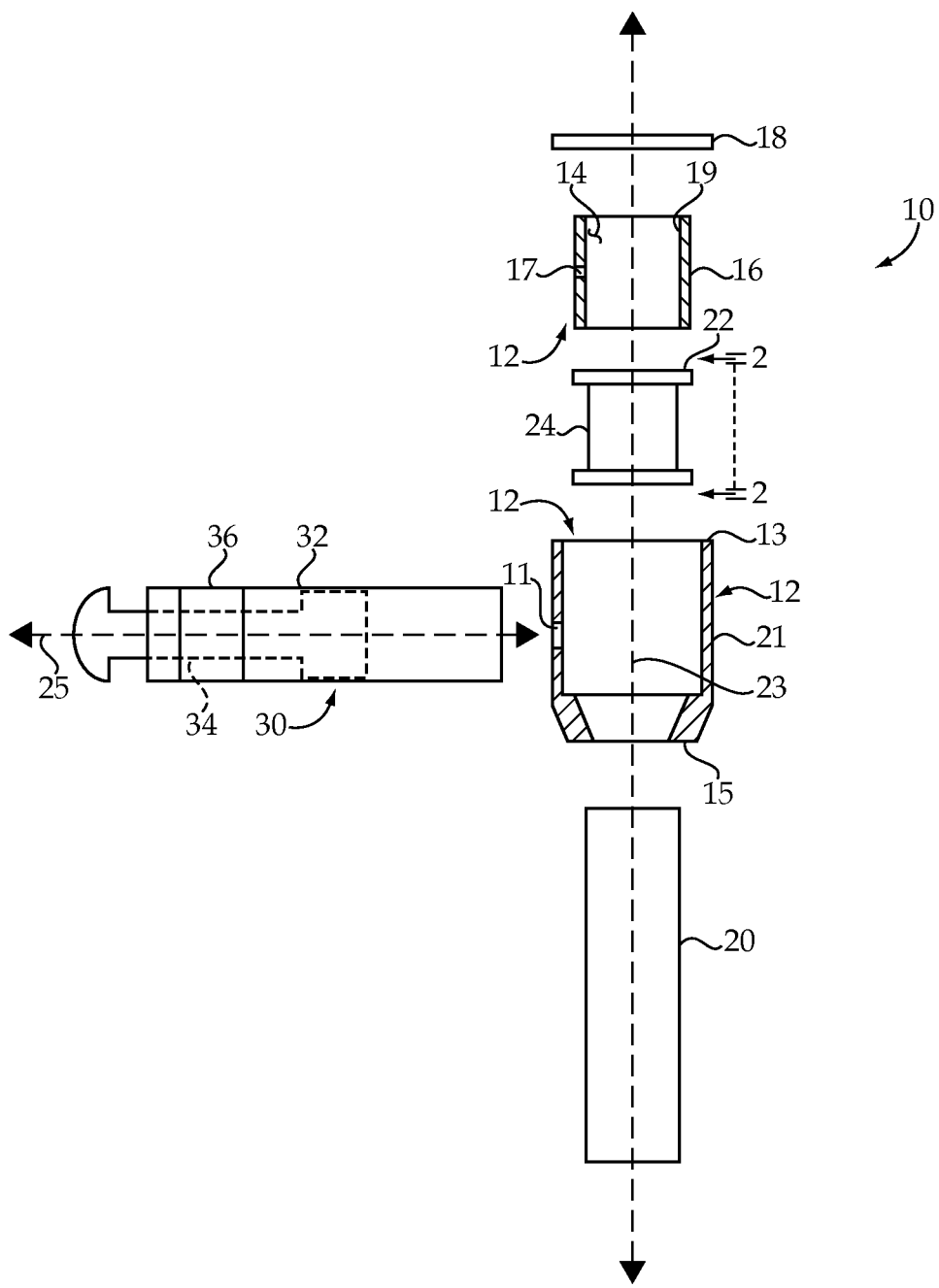
FIG. 1 is a disassembled view of a hemostasis mechanism, with certain components sectioned, according to one embodiment.

Referring to FIG. 1, there is shown a hemostasis mechanism 10 for use in treating a patient, according to one embodiment. Mechanism 10 includes a housing 12 defining a through-bore 14 having a longitudinal axis 23, and a port 11 in fluid communication with through-bore 14. Housing 12 may include a multi-piece housing in certain embodiments, and having an outer housing piece 21 and a core piece 16. Housing 12 may also include a cap 18 attached to outer piece 21 and configured to clamp core piece 16 and a pressure responsive seal 22 within outer piece 21. In an assembled state, pressure responsive seal 22 extends circumferentially about longitudinal axis 23 within through-bore 14, and includes an outer seal surface 24 exposed to a fluid pressure of port 11, and an inner seal surface 26. Housing 12 may also include a tube piece 20 configured to attach to outer housing piece 21 such that through-bore 14 may be placed in fluid communication with a body lumen in a patient, as further described herein. As will be further apparent from the following description, the present disclosure sets forth unique design and methodology for controlling sealing engagement of pressure responsive seal 22 about a transluminal device positioned within through-bore 14 and extending through mechanism 10 into a body lumen of a patient such as a vein or artery.

Mechanism 10 also includes a pressurization device 30 in fluid communication with port 11, and including a plunger 34 movable from a first position approximately as shown in FIG. 1, toward an advanced position, to increase a fluid pressure of port 11 such that seal 22 deforms into sealing engagement with a transluminal device. Device 30 further includes a detent 36 operably coupled with plunger 34 and having a release state, and an engaged state holding plunger 34 at an advanced position to maintain the increased fluid pressure. In the illustrated embodiment, when mechanism 10 is assembled core piece 16 will be positioned within outer housing piece 21, and port 17 will be placed in fluid communication with port 11 such that ports 11 and 17 together communicate a fluid pressure of pressurization device 30 to seal 22. In alternative embodiments, housing pieces 21 and 16 could be formed as a single piece having a single port. Core piece 16 includes an inner housing surface 19 defining through-bore 14. Where no core piece is used, the single housing piece taking the place of outer housing piece 21 and core piece 16 could be understood to include the inner housing surface defining the through-bore.

Figure 2:
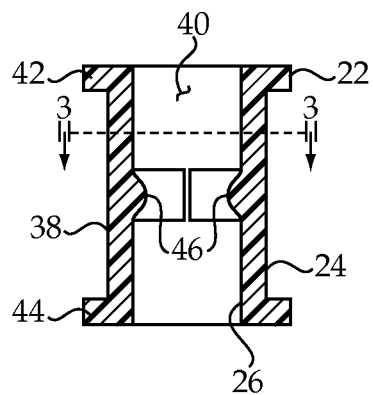
FIG. 2 is a sectioned view taken along line 2-2 of FIG. 1.

Referring now to FIG. 2, there is shown a sectioned view through seal 22 taken along line 2-2 of FIG. 1. Seal 22 may be formed of a suitable deformable material such as a rubber-like material or silicone, and may have a cylindrical wall 38 which includes inner seal surface 26 and outer seal surface 24, cylindrical wall 38 having a longitudinal passage 40 formed therein for receipt of a transluminal device and being co-axial with through-bore 14 when mechanism 10 is assembled for receipt of a transluminal device. Seal 22 may further include a first end flange 42 and a second end flange 44, each projecting radially outward from cylindrical wall 38. When mechanism 10 is assembled, core piece 16 may be positioned about cylindrical wall 38 between first and second end flanges 42 and 44. Outer piece 21 may contain seal 22 and core piece 16 therein, and cap 18 may be attached to outer piece 21 and clamps core piece 16 and seal 22 within outer piece 21. Cap 18 might be attached to outer piece 21 via an adhesive, threads, or an interference fit or the like, such that first end flange 42 is compressed and held in sealing engagement between cap 18 and core piece 16, and second end flange 44 is compressed and held in sealing engagement between outer piece 21 and core piece 16, the significance of which will be further apparent from the following description and illustrated by way of subsequently described drawings.

Figure 3:
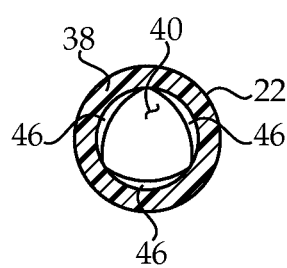
FIG. 3 is a sectioned view taken along line 3-3 of FIG. 2.
Figure 4:
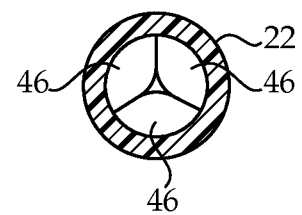
FIG. 4 is another sectioned view similar to FIG. 3.

Referring also now to FIG. 3, there is shown a sectioned view taken along line 3-3 of FIG. 2, and illustrating a plurality of sealing protrusions 46 each projecting radially inward from cylindrical wall 38 and being movable inwardly via the pressure responsive deformation of seal 22 to establish the sealing engagement of seal 22 with the transluminal device. In the embodiment shown, sealing protrusions 46 are crescent shaped, and a total of three such sealing protrusions 46 are provided. Upon deforming seal 22, and in particular deforming cylindrical wall 38 inwardly in response to a fluid pressure supplied from pressurization device 30, protrusions 46 form a tricuspid sealing pattern about the transluminal device extending through passage 40 and through-bore 14. FIG. 4 illustrates an example tricuspid sealing pattern.

Figure 5:
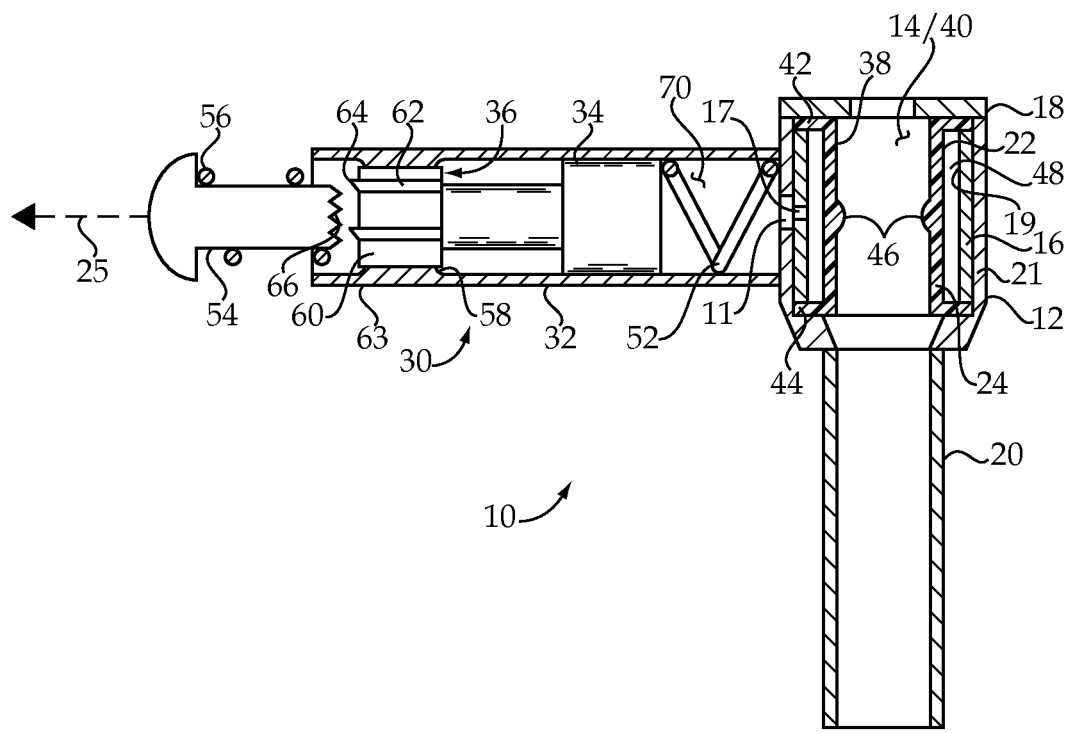
FIG. 5 is a sectioned side diagrammatic view of the hemostasis mechanism of FIG. 1, in an assembled state.

Referring now also to FIG. 5, there is shown mechanism 10 assembled, where cap 18 is attached to outer piece 21 and clamps core piece 16 and seal 22 therein. Tube 20 is attached to outer housing piece 21, and pressurization device 30 is also attached to outer piece 21 such that a cavity 70 formed in a housing 32 of pressurization device 30 is in fluid communication with port 11, port 17, and a clearance 48 which extends between inner housing surface 19 and outer seal surface 24 and surrounds seal 22. Fluid communication between clearance 48 and cavity 70 via ports 11 and 17 allows a pressure of a fluid, such as air, or saline, to act upon seal 22 to deform the same, thereby controlling the sealing engagement between seal 22 and a transluminal device extending through mechanism 10. In one embodiment, pressurization device 30 further includes a biasing spring 52 positioned within cavity 70 and biasing plunger 34 toward the first position, approximately as shown in FIG. 5. Pressurization device 30 may further include a plunger actuator 54 coupled with plunger 34, and which could be formed as one piece therewith, configured to control advancing and retracting of plunger 34 to vary fluid pressure in cavity 70 and thereby control the sealing engagement of seal 22. Actuator 54 may include a button or the like configured to be pushed by a clinician to advance and retract plunger 34, and also to adjust detent 36 between its engaged state and its release state as further described herein.

It will be recalled that in the release state of detent 36, plunger 34 may be retracted, such as under the influence of spring 52, and also under the influence of a fluid pressure in cavity 70. In the engaged state of detent 36, plunger 34 will be held at its advanced position to maintain an increased pressure in cavity 70, and thereby maintain sealing engagement of seal 22 about the transluminal device. In certain embodiments, pushing actuator 54 may push plunger 34 to advance the same, and simultaneously adjust detent 36 to its release state or its engaged state, as the case may be. A biasing spring 56 may be positioned between actuator 54 and housing 32 to bias actuator 54 away from and out of contact with plunger 34. Any suitable retention mechanism might be employed to prevent actuator 54 from popping out of housing 32 if desired.

A variety of different detent designs are contemplated herein, and in a practical implementation strategy detent 36 may function in a manner analogous to that of detents used in connection with certain ball point pens. To this end, plunger 34 may define a transverse axis 25, and detent 36 may further include a non-rotatable stop 58, formed integrally with housing 32 for example, and a rotatable catch 60 coupled with plunger 34. Catch 60 may be movable between a first angular orientation about transverse axis 25 at which catch 60 contacts stop 58 and retracting of plunger 34 from its advanced position is prevented, and a second orientation at which refracting of plunger 34 is permitted.

In FIG. 5, detent 36 is shown in its release state such that catch 60 is not engaged with stop 58 and plunger 34 has moved to a first, retracted position via spring 52. In particular, a plurality of ribs 62 of catch 60 have been permitted to slide past a plurality of counterpart ribs 63 of stop 58. Catch 60 is thus at an example second orientation about axis 25. Ribs 62 may each include an angled end surface 64 which is engaged by counterpart angled end surfaces 66 on the end of actuator 54. Sliding engagement between end surfaces 66 and 64 as actuator 54 is advanced, in opposition to a force of spring 56, can impart a tendency for catch 60 to rotate about axis 25 to a position at which ribs 62 contact ribs 63. Since catch 62 is coupled with plunger 34, and may be attached to plunger 34, when ribs 62 are rotated to a position at which they engage ribs 63, plunger 34 is held in an advanced position. In particular, facing end surfaces of the respective ribs may contact one another to inhibit axial sliding of catch 60 and plunger 34 to the left in FIG. 5.

INDUSTRIAL APPLICABILITY

Figure 6:
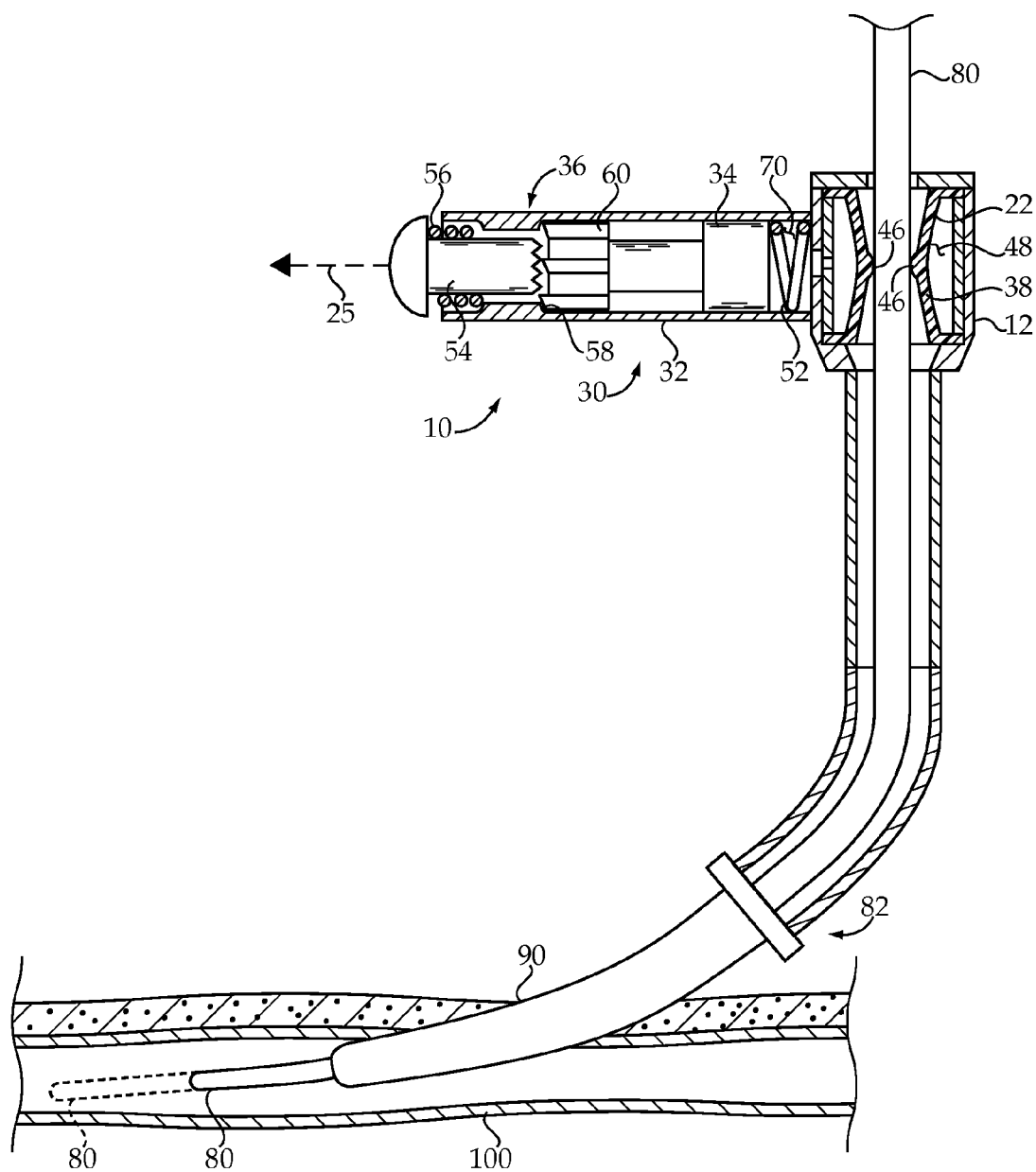
FIG. 6 is a partially sectioned side diagrammatic view of the hemostasis mechanism of FIG. 1 at one stage of a treatment procedure, according to one embodiment.

Referring now also to FIG. 6, there is shown mechanism 10 as it might appear with a transluminal device 80 extending therethrough, and into a patient via an introducer 82 providing an entry point 90 into a body lumen 100 of the patient. In FIG. 6, plunger 34 has been pushed toward an advanced positioned in pressurization device 30 by pushing actuator 54. Actuator 54 has interacted with catch 60 to rotate catch 60 to its first angular orientation at which it contacts stop 54 such that retracting of plunger 34 from its advanced position is prevented. In response to pushing plunger 34, detent 36 has thus been adjusted to its engaged state inhibiting retracting of plunger 34. Fluid pressure in cavity 70 has thus increased to supply an increased fluid pressure to clearance 48. Seal 22, and in particular cylindrical wall 38, has deformed in response to the increased pressure such that sealing protrusions 46 contact transluminal device 80.

Sealing about transluminal device 80, which may include a catheter, wire guide, or some other mechanism, in this general manner may be performed for various purposes such as the injection of fluid into the body lumen, to prevent backflow of the fluid during injecting, or simply to prevent blood from the body lumen from flowing back through the apparatus providing percutaneous access. In the case of fluid injections, a side arm fitting or the like might be coupled with mechanism 10 or introducer 82 to enable a second fluid access path into body lumen 100. When it is desirable to change a position of device 80 within body lumen 100, actuator 54 may be pushed again to adjust detent 36 from its engaged state inhibiting retracting of plunger 34, to its release state. It will thus be appreciated that plunger 34 may be slightly advanced within housing 32 when actuator 54 is pushed to release detent 36. When detent 36 is adjusted to its release state, plunger 34 may retract such that fluid pressure supplied by device 30 to seal 22 is reduced. The fluid pressure in cavity 70, and an expanding force of spring 52, may urge plunger 34 back toward its retracted position with detent 36 released. The reduced pressure in clearance 48 will reduce the sealing force of seal 22 about transluminal device 80. This facilitates sliding of transluminal device 80 to a changed position within body lumen 100, while the pressure in clearance 48 is at a reduced pressure such as the position shown via phantom lines in FIG. 6. When it is again desirable to seal about transluminal device 80, a clinician may reestablish sealing engagement of seal 22 about device 80 at a changed position, and adjust detent 36 back to its engaged state to maintain the reestablished sealing engagement, in response to another pushing of actuator 54 and thus plunger 34 toward an advanced position.

As noted about, known hemostasis mechanism suffer from a variety of drawbacks. In the case of certain pressure actuated hemostasis mechanisms, one drawback is commonly the need to manually maintain a pressure about a hemostasis seal. In the present disclosure, a clinician may let go of plunger 34, in particular letting go of actuator 54, subsequent to adjusting detent 36 to, or back to, its engaged state. Another shortcoming associated with certain known hemostasis mechanisms is the lack of any positive feedback to a clinician indicating that a seal has been established about a transluminal device. In other words, a clinician will often have no way to know whether the seal formed about a transluminal device is sufficient, but instead relies upon guesswork or experience to determine whether they have supplied sufficient pressure to hold the seal. In the present disclosure, the relatively simple push-button operation of pressurization device 30 allows both hands-free work while the seal is established, and also tactile feedback to the clinician that indicates positive sealing engagement. In other words, the clinician will typically be able to feel the click when detent 36 is adjusted to its engaged state, and also feel a click when detent 36 is adjusted to its release state. Still another feature contemplated to be superior to known designs relates to the capability of pulling open seal 22 via reduced pressure resulting from retracting plunger 34. In other words, a relatively rapid decrease in pressure within clearance 48 can impart a tendency for seal 22 to pop open relatively rapidly, hastening certain aspects of the associated treatment procedure. While it is contemplated that the fluid displaced by plunger 34 to control seal 22 will typically be air, for instance a displacement of about 2 milliliters of air, the present disclosure is not thereby limited and as alluded to above saline or some other actuation fluid might instead be used. It should also be appreciated that while pressurization device 30 is shown attached to housing 12, in other instances a separate pressurization device connected via a flexible conduit or the like might be used.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A hemostasis mechanism for use in treating a patient comprising:
    a housing defining a through-bore having a longitudinal axis, and a first port in fluid communication with the through-bore;
    a pressure responsive seal extending circumferentially about the longitudinal axis within the through-bore, and having an outer seal surface exposed to a fluid pressure of the first port, and an inner seal surface;
    a pressurization device in fluid communication with the first port, and including a plunger movable from a first position toward an advanced position, to increase the fluid pressure such that the pressure responsive seal deforms into sealing engagement with a transluminal device positioned within the through-bore;
    the pressurization device further including a detent operably coupled with the plunger and having a release state, and an engaged state holding the plunger at the advanced position to maintain the increased fluid pressure; and
    the housing further includes a core piece having the first port formed therein and positioned about the cylindrical wall between the first and second end flanges, and an outer piece containing the pressure responsive seal and the core piece and having a second port formed therein fluidly connecting the first port with the pressurization device.

2. The mechanism of claim 1 wherein the plunger defines a transverse axis, and the detent further includes a non-rotatable stop, and a rotatable catch coupled with the plunger and movable between a first angular orientation about the transverse axis at which the catch contacts the stop and retracting of the plunger from the advanced position is prevented, and a second orientation at which retracting of the plunger is permitted.

3. The mechanism of claim 1 wherein the housing includes an inner housing surface defining the through-bore, and a clearance in fluid communication with the port extends between the inner housing surface and the outer seal surface and surrounds the pressure responsive seal.

4. The mechanism of claim 3 wherein the pressure responsive seal includes a cylindrical wall including the inner and outer seal surfaces, and having a longitudinal passage formed therein and being coaxial with the through-bore, for receipt of the transluminal device.

5. The mechanism of claim 4 wherein the pressure responsive seal further includes a first end flange and a second end flange, each projecting radially outward from the cylindrical wall.

6. The mechanism of claim 4 wherein the pressure responsive seal further includes a plurality of sealing protrusions each projecting radially inward from the cylindrical wall and being movable inwardly via the deformation to establish the sealing engagement with the transluminal device.

7. The mechanism of claim 6 wherein the plurality of sealing protrusions includes a total of three crescent shaped protrusions forming a tricuspid sealing pattern about the transluminal device.

8. The mechanism of claim 3 further comprising a biasing spring biasing the plunger toward the first position.

9. The mechanism of claim 8 wherein the plunger defines a transverse axis, and the detent further includes a non-rotatable stop, and a rotatable catch coupled with the plunger and movable between a first angular orientation about the transverse axis at which the catch contacts the stop and retracting of the plunger from the advanced position is prevented, and a second orientation at which retracting of the plunger is permitted.

10. The mechanism of claim 1 wherein the housing further includes a cap attached to the outer piece and clamping the core piece and the pressure responsive seal within the outer piece, such that the first end flange is held in sealing engagement between the cap and the core piece, and the second end flange is held in sealing engagement between the outer piece and the core piece, to fluidly isolate the clearance from the through-bore.

11. A method of percutaneously treating a patient with a hemostasis mechanism that includes a housing defining a through-bore having a longitudinal axis, and a first port in fluid communication with the through-bore; a pressure responsive seal extending circumferentially about the longitudinal axis within the through-bore, and having an outer seal surface exposed to a fluid pressure of the first port, and an inner seal surface; a pressurization device in fluid communication with the first port, and including a plunger movable from a first position toward an advanced position, to increase the fluid pressure such that the pressure responsive seal deforms into sealing engagement with a transluminal device positioned within the through-bore; and the pressurization device further including a detent operably coupled with the plunger and having a release state, and an engaged state holding the plunger at the advanced position to maintain the increased fluid pressure, the housing further includes a core piece having the first port formed therein and positioned about the cylindrical wall between the first and second end flanges, and an outer piece containing the pressure responsive seal and the core piece and having a second port formed therein fluidly connecting the first port with the pressurization device, the method comprising the steps of:

pushing the plunger toward the advanced position in the pressurization device in fluid communication with the pressure responsive seal of the hemostasis mechanism in sealing engagement with the transluminal device;

adjusting the detent in the pressurization device from the engaged state inhibiting retracting of the plunger, to the release state, in response to the pushing of the plunger;

retracting the plunger subsequent to adjusting the detent such that a fluid pressure supplied by the pressurization device to the pressure responsive seal is reduced; and sliding the transluminal device through the hemostasis mechanism to change its position within a body lumen of the patient while the fluid pressure is at the reduced pressure.

12. The method of claim 11 wherein the step of retracting includes retracting the plunger under the influence of a biasing spring.

13. The method of claim 12 further comprising a step of pulling open the pressure responsive seal via the reduced pressure.

14. The method of claim 12 further comprising the steps of reestablishing sealing engagement of the pressure responsive seal about the transluminal device at its changed position, and adjusting the detent back to its engaged state to maintain the reestablished sealing engagement, in response to pushing the plunger again.

15. The method of claim 14 further comprising a step of letting go of an actuator for the plunger subsequent to the adjustment of the detent back to its engaged state.

16. The method of claim 14 wherein the step of reestablishing includes deforming the pressure responsive seal to a tricuspid sealing pattern.

17. The method of claim 14 wherein the step of reestablishing includes displacing about 2 milliliters of air during the another advancement of the plunger.

* * * * *